(12) United States Patent
Ni et al.

(10) Patent No.: US 11,998,326 B2
(45) Date of Patent: *Jun. 4, 2024

(54) SMART WEARABLE DEVICE (71) Applicant: HUAWEI TECHNOLOGIES CO., LTD., Guangdong (CN)

(72) Inventors: Xiaodong Ni, Shenzhen (CN); Yi Xi, Dongguan (CN); Ao Shen, Grenoble (FR); Wenxiong Wei, Hangzhou (CN)

(73) Assignee: Huawei Technologies Co., Ltd., Shenzhen (CN)

(*) Notice: Subject to any disclaimer, the term of this patent is extended or adjusted under 35 U.S.C. 154(b) by 130 days.

This patent is subject to a terminal disclaimer.

(21) Appl. No.: 17/585,841

(22) Filed: Jan. 27, 2022

(65) Prior Publication Data

US 2022/0142489 A1 May 12, 2022

Related U.S. Application Data

(63) Continuation of application No. 16/346,743, filed as application No. PCT/CN2017/070888 on Jan. 11, 2017, now Pat. No. 11,272,846.

(30) Foreign Application Priority Data

Nov. 2, 2016 (CN) .......................... 201610945334.5

(51) Int. Cl.
*A61B 5/0205* (2006.01)
*A61B 5/00* (2006.01)
(Continued)

(52) U.S. Cl.
CPC ........ *A61B 5/14552* (2013.01); *A61B 5/0205* (2013.01); *A61B 5/25* (2021.01);
(Continued)

(58) Field of Classification Search
CPC ...... A61B 5/0205; A61B 5/25; A61B 5/14552
See application file for complete search history.

(56) References Cited

U.S. PATENT DOCUMENTS

2009/0163784 A1* 6/2009 Sarpeshkar ............. H03F 1/342
330/98
2009/0230777 A1 9/2009 Baarman et al.
(Continued)

FOREIGN PATENT DOCUMENTS

| CA | 2466105 | 6/2012 |
| CN | 202874035 | 4/2013 |

(Continued)

OTHER PUBLICATIONS

Anonymous [online], "Apple patent: Let Apple Watch monitor heart rate more accurately," retrieved from internet on Oct. 7, 2019, retrieved from URL <http://www.keke289.com/news/145482.html>, 4 pages (partial English translation).
(Continued)

*Primary Examiner* — Nadia A Mahmood
(74) *Attorney, Agent, or Firm* — Fish & Richardson P.C.

(57) ABSTRACT

A smart wearable device includes a detection apparatus and a case, the detection apparatus specifically includes one set of measuring parts and a plurality of sets of light emitting parts; the one set of measuring parts and the plurality of sets of light emitting parts are inlaid into the case and arranged into a polygon, where each of the plurality of sets of light emitting parts and the one set of measuring parts each occupies one of a plurality of angles of the polygon, and a central position of the polygon is at a specified distance to each angle of the polygon. A specific embodiment of the present invention provides a smart wearable device. One set of measuring parts and a plurality of sets of light emitting parts are disposed into a case and arranged into a polygon.

20 Claims, 6 Drawing Sheets

(51) Int. Cl.
*A61B 5/1455* (2006.01)
*A61B 5/25* (2021.01)
*G06F 1/16* (2006.01)
*A61B 5/024* (2006.01)
*H02J 50/10* (2016.01)

(52) U.S. Cl.
CPC .............. *A61B 5/681* (2013.01); *G06F 1/163* (2013.01); *A61B 5/02416* (2013.01); *A61B 5/02438* (2013.01); *A61B 2560/0209* (2013.01); *A61B 2560/0214* (2013.01); *H02J 50/10* (2016.02)

(56) References Cited

U.S. PATENT DOCUMENTS

| | | |
|---|---|---|
| 2014/0073486 A1 | 3/2014 | Ahmed et al. |
| 2014/0221848 A1 | 8/2014 | Nagasaka |
| 2015/0099941 A1 | 4/2015 | Tran |
| 2015/0148636 A1 | 5/2015 | Benaron |
| 2015/0157220 A1 | 6/2015 | Fish et al. |
| 2016/0174854 A1 | 6/2016 | Nishida et al. |
| 2017/0055861 A1 | 3/2017 | Narusawa et al. |
| 2017/0100038 A1 | 4/2017 | Narusawa |

FOREIGN PATENT DOCUMENTS

| | | |
|---|---|---|
| CN | 103549944 | 2/2014 |
| CN | 203564224 | 4/2014 |
| CN | 103961080 | 8/2014 |
| CN | 104367310 | 2/2015 |
| CN | 104392103 | 3/2015 |
| CN | 104414625 | 3/2015 |
| CN | 104814745 | 8/2015 |
| CN | 104939811 | 9/2015 |
| CN | 105208924 | 12/2015 |
| CN | 105249931 | 1/2016 |
| CN | 205041396 | 2/2016 |
| CN | 105446126 | 3/2016 |
| CN | 105549683 | 5/2016 |
| CN | 105708434 | 6/2016 |
| CN | 205338940 | 6/2016 |
| CN | 105978075 | 9/2016 |
| CN | 107708557 | 2/2018 |
| EP | 1970000 | 9/2008 |
| EP | 2839778 | 2/2015 |
| EP | 3033990 | 6/2016 |
| JP | 2004081285 | 3/2004 |
| JP | 2004515274 | 5/2004 |
| JP | 2011517926 | 6/2011 |
| JP | 2016112277 | 6/2016 |
| KR | 20080083505 | 9/2008 |
| KR | 20130010797 | 1/2013 |
| KR | 101343883 B1 | 12/2013 |
| KR | 20160047964 | 5/2016 |
| KR | 102442744 B1 | 9/2022 |
| WO | WO2014066791 | 5/2014 |
| WO | WO2015150199 | 10/2015 |
| WO | WO2016032682 | 3/2016 |

OTHER PUBLICATIONS

Extended European Search Report issued in European Application No. 17867213.5 dated Aug. 5, 2019, 7 pages.
Office Action issued in Chinese Application No. 201780003527.1 dated Aug. 19, 2019, 9 pages.
Office Action issued in Chinese Application No. 201780003527.1 dated Jul. 10, 2020, 21 pages (with English translation).
Office Action issued in Chinese Application No. 202110253779.8 dated Nov. 3, 2021, 8 pages.
Office Action issued in Indian Application No. 201947018404 dated Mar. 12, 2021, 5 pages.
Office Action issued in Japanese Application No. 2019523806 dated May 18, 2020, 7 pages (With English Translation).
Office Action issued in Korean Application No. 2019-7015194 dated Nov. 30, 2020, 11 pages (with English translation).
Office Action issued in Korean Application No. 2021-7031274 dated Dec. 27, 2021, 12 pages (with English translation).
PCT International Search Report and Written Opinion issued in International Application No. PCT/CN2017/070888 dated Jul. 4, 2017, 17 pages (with English translation).
EPO Communication pursuant to Article 94(3) EPC issued in European Application No. 17867213.5 dated May 27, 2022, 6 pages.
Chen et al., "Anthropomorphic corporate life exploration," Publishing China Financial Press, May 1, 2015, 5 pages (with an English abstract).
Office Action in Chinese Appln. No. 202110253779.8, dated Aug. 10, 2022, 12 pages.
Office Action in Korean Appln. No. 10-2022-7030868, dated May 30, 2023, 7 pages (with English translation).
Request for Oral Hearing in Indian Appln. No. 201947018404, mailed on Aug. 1, 2023, 2 pages (with English translation).

* cited by examiner

SMART WEARABLE DEVICE

CROSS-REFERENCE TO RELATED APPLICATIONS

This application is a continuation of U.S. patent application Ser. No. 16/346,743, filed on May 1, 2019, which is a national stage of International Application No. PCT/CN2017/070888, filed on Jan. 11, 2017, which claims priority to Chinese Patent Application No. 201610945334.5, filed on Nov. 2, 2016. All of the aforementioned Applications are hereby incorporated by reference in their entireties.

TECHNICAL FIELD

The present invention relates to the field of wearable device technologies, and in particular, to a smart wearable device.

BACKGROUND

Heart rate detection is an important function of a current wearable device. At present, a photoplethysmograph (PPG) method and an electrocardiogram (ECG) method are used for most heart rate detection. The ECG method is characterized by accurate measurement but requires that a test be conducted near a heart or at a plurality of points. The PPG method requires only single-point measurement and therefore has lower measurement accuracy than the PPG method.

In the prior art, smart wearable devices are increasingly used in daily life. Functions of the smart wearable devices are also increasingly abundant, and usually include such an item as heart rate detection. Currently, watches, bands, and finger-clip measuring instruments generally use a PPG-method-based measurement solution because the PPG method is convenient.

The PPG includes a transmissive mode and a reflective mode, and the reflective mode is usually used for wearable devices. A basic principle of the reflective mode is: A light emitting diode (LED) emits light; the light is reflected by hemoglobin in a blood vessel inside a human tissue; and the reflected light is received by a photodiode (PD). In the reflected light, a major portion is a direct current (DC) signal and a minor portion is an alternating current (AC) signal resulting from pulsing. Because content of hemoglobin and the like are related to the human pulse, a PPG system detects the light collected by the PD and calculates an oxygen saturation, so as to determine a detection result. Specifically, the alternating current signal is a key signal for detecting blood oxygen or a heart rate.

A common smartwatch includes a straight-line single-PD solution. Specifically, a PD is disposed in the middle and LEDs are disposed at both sides. Such a layout is compact and highly efficient in light utilization, and is used by most PPGs at present. However, in this solution, the PD needs to be disposed in the middle of a device, and a distance between the LEDs and the PD is excessively small. These two restrictions lead to a conflict in designing a wireless charging function and the like for the device and an insufficient modulation depth.

SUMMARY

Embodiments of the present invention provide a smart wearable device, so as to increase a modulation depth of a detection result of a detection apparatus, and leave a central position of a case vacant to accommodate another device.

According to a first aspect, a specific embodiment of the present invention provides a smart wearable device, where the smart wearable device includes a detection apparatus and a case, the detection apparatus specifically includes one set of measuring parts and a plurality of sets of light emitting parts; the one set of measuring parts and the plurality of sets of light emitting parts are disposed into the case and arranged into a polygon, where each of the plurality of sets of light emitting parts and the one set of measuring parts each occupies one of a plurality of angles of the polygon, and a central position of the polygon is at a specified distance to each angle of the polygon. This can enlarge a distance between the one set of measuring parts and the plurality of sets of light emitting parts, so as to increase a modulation depth of the device.

In a possible design, a second device is further disposed at the central position of the case. Disposing the second device at the central position of the case enables the second device to have a better use effect.

In a possible design, the smart wearable device further includes a wireless charging device, the wireless charging device includes an electromagnetic coil and a magnet, the electromagnetic coil is disposed at an edge of the case, and the magnet is the second device. Disposing the wireless charging device in the smart wearable device and disposing the magnet of the wireless charging device at the central position of the case improve charging efficiency of the wireless charging device.

In a possible design, the second device is an electrode for electrocardiograph measurement. Disposing the electrode for electrocardiograph measurement at the central position of the case makes a result of electrocardiograph measurement more approximate to an actual value.

In a possible design, the one set of light emitting parts includes at least one light emitting diode, and the one set of measuring parts includes at least one photodiode. Disposing a plurality of light emitting diodes in the one set of light emitting parts and/or disposing a plurality of photodiodes in the one set of measuring parts improve/improves effectiveness of the detection apparatus.

In a possible design, the polygon is a quadrilateral, and the quadrilateral consists of a first set of measuring parts, a first set of light emitting parts, a second set of light emitting parts, and a third set of light emitting parts, where the first set of light emitting parts and the second set of light emitting parts are adjacent to the first set of measuring parts, the third set of light emitting parts are opposite to the first set of measuring parts, and the third set of light emitting parts are adjacent to the first set of light emitting parts and the second set of light emitting parts.

In a possible design, the first set of light emitting parts and the second set of light emitting parts are each at least one green diode, and the third set of light emitting parts is at least one red/infrared diode.

In a possible design, the third set of light emitting parts is at least one green diode, and the first set of light emitting parts and the second set of light emitting parts are each at least one red/infrared diode.

In a possible design, the first set of light emitting parts, the second set of light emitting parts, and the third set of light emitting parts are light emitting diodes of a same color; and the smart wearable device starts the first set of light emitting parts and the second set of light emitting parts according to a first control signal, and starts the third set of light emitting parts according to a second control signal, where the first control signal is a signal for reducing system power consumption, and the second control signal is a signal for increasing a modulation depth.

In a possible design, the first set of light emitting parts, the second set of light emitting parts, and the third set of light emitting parts are tri-color light emitting diodes of red, infrared, and green; and the smart wearable device starts the first set of light emitting parts and the second set of light emitting parts according to a first control signal or a third control signal, and starts the third set of light emitting parts according to a second control signal or a fourth control signal, where the first control signal is a blood oxygen detection signal for reducing system power consumption, the second control signal is a blood oxygen detection signal for increasing a modulation depth, the third control signal is a heart rate detection signal for reducing system power consumption, and the fourth control signal is a heart rate detection signal for increasing a modulation depth.

In a possible design, the first set of measuring parts includes at least one photodiode.

In a possible design, the smart wearable device is a smartwatch.

The specific embodiment of the present invention provides a smart wearable device. The one set of measuring parts and the plurality of sets of light emitting parts are disposed into the case and arranged into a polygon. This enlarges the distance between the one set of measuring parts and the plurality of sets of light emitting parts of the smart wearable device, so as to increase the modulation depth of the detection result of the measuring parts. In addition, the central position of the case is left vacant to accommodate another device.

DESCRIPTION OF EMBODIMENTS

The technical solutions in the embodiments of the present invention are further described in detail with reference to the accompanying drawings and the embodiments.

It may be understood that descriptions of technical features, beneficial effects, or similar statements in the specification do not imply that all the technical features and beneficial effects can be implemented in any single embodiment. To the contrary, it may be understood that a statement about a technical feature or a beneficial effect indicates that at least one embodiment includes the particular technical feature or beneficial effect. Therefore, the descriptions of technical features, beneficial effects, or similar statements in the specification do not necessarily refer to a same embodiment. In addition, the technical features or beneficial effects described in the embodiments may be combined in any proper manner. A person skilled in the art may understand that a particular embodiment can be implemented without one or more particular technical features or beneficial effects of the embodiment.

Figure 1:
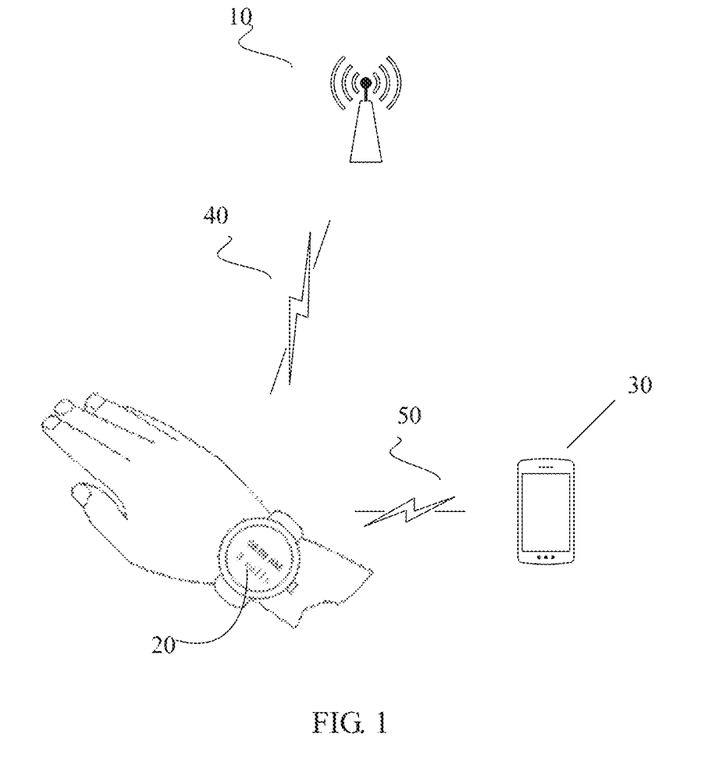
FIG. 1 is a diagram of an application environment of a smart wearable device according to a specific embodiment of the present invention.

FIG. 1 is a diagram of an application environment of a smart wearable device according to a specific embodiment of the present invention. As shown in FIG. 1, this embodiment of the present invention relates to a smart wearable device 20. The smart wearable device 20 may perform wireless communication with a network-side base station 10 or a mobile phone 30 in a wireless manner. For example, the smart wearable device may send a radio signal to the network-side base station 10 by using a radio frequency circuit and an antenna of the smart wearable device and through a radio communications link 40, to request the network-side base station 10 to perform a radio network service so as to process a specific service requirement of the smart wearable device 20. For another example, the smart wearable device 20 may pair with the mobile phone 30 by using Bluetooth of the smart wearable device 20. After pairing is successful, the smart wearable device 20 performs data communication with the mobile phone by using a Bluetooth communications link 50. Certainly, the smart wearable device 20 may perform data communication with the mobile phone in another wireless communications manner, such as a radio frequency identification technology or a short-range wireless communications technology. In addition, the smart wearable device 20 may further detect an external environmental change by using various sensors of the smart wearable device 20.

In this specific embodiment of the present invention, the smart wearable device may be a plurality of types of devices. In an example, the smart wearable device may be any one of a smartwatch, a smart band, and another smart wearable device. For ease of description, only the smartwatch is used as an example for specific descriptions in specific embodiments of the present invention.

Figure 2:
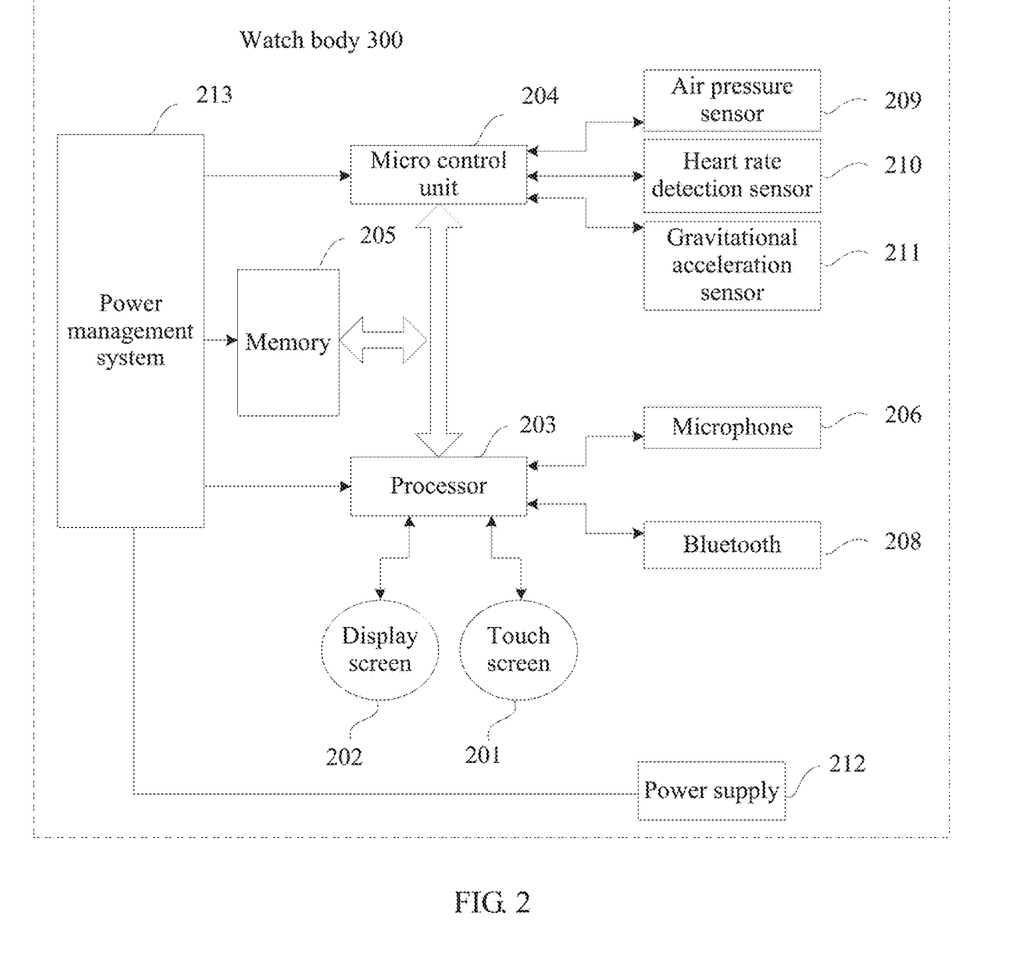
FIG. 2 is a schematic diagram of a hardware structure of a smartwatch according to an embodiment of the present invention.

FIG. 2 is a schematic diagram of a hardware structure of a smartwatch according to an embodiment of the present invention. The smartwatch may include a watch body 300.

For example, as shown in FIG. 2, the watch body 300 may include a touchscreen 201 (also referred to as a touchscreen), a display screen 202, a case (the case includes a front case (not shown in FIG. 2) and a bottom case (not shown in FIG. 2), a processor 203, a micro control unit (MCU) 204, a power management system 213, a memory 205, a microphone (MIC) 206, a Bluetooth (BT) 208, an air pressure detection apparatus 209 (e.g. air pressure sensor), a heart rate detection apparatus 210, a gravitational acceleration sensor 211, a power supply 212, a power management system 213, and the like.

Although not shown, the watch body 300 may further include an antenna, a wireless-fidelity (WiFi) module, a near field communication (NFC) module, a Global Positioning System ((IPS) module, a loudspeaker, an accelerometer, a gyroscope, and the like. A watch band component 400 may further include the power supply 212 (such as a battery) that supplies power to all the components. Preferably, the power supply 212 may be logically connected to the processor 203 by using the power management system 213, so as to implement functions such as charge management, discharge management, and power consumption management by using the power management system 213.

The following introduces the function components of the smartwatch separately.

The touchscreen 201 is also referred to as a touch panel, and is capable of collecting a touch operation of a user on the touchscreen 201 (such as an operation performed by the user on the touch panel or near the touch panel with a finger, a stylus, or any suitable object or accessory), and driving a corresponding connection apparatus according to a preset program.

The display screen 202 may be configured to display information input by the user or information provided to the user, and various menus of the watch. Further, the touchscreen 201 may cover the display screen 202. After detecting a touch operation on or near the touchscreen 201, the touchscreen 201 sends the touch operation to the processor 203 to determine a type of a touch event. Then the processor 203 provides corresponding visual output on the display screen 202 according to the type of the touch event.

The processor 203 is configured to perform system scheduling, control the display screen and the touchscreen, and support work of the microphone 206 and the Bluetooth 208.

The microphone 206 is also referred to as a mike. The microphone 206 may transform a collected sound signal into an electrical signal. An audio circuit receives the electrical signal, and then transforms the electrical signal into audio data. The audio circuit may also transform audio data into an electrical signal and transmit the electrical signal to a loudspeaker, and the loudspeaker transforms the electrical signal into a sound signal for output.

The Bluetooth 208 allows the smartwatch to exchange information with another electronic device (such as a mobile phone or a tablet computer) by using the Bluetooth. By using the electronic device, the smartwatch, for example, connects to a network, connects to a server, and processes speech recognition.

The micro control unit 204 is configured to, for example, control a sensor, perform computation on sensor data, and communicate with the processor 203. The sensor may be the air pressure detection apparatus 209, the heart rate detection apparatus 210, the gravitational acceleration sensor 211, a light sensor, a motion sensor, or another sensor.

The memory 205 is configured to store a software program and data. The processor 203 executes various function applications and data processing of the smartwatch by running the software program and data that are stored in the memory 205.

It should be noted that the foregoing hardware function components of the smartwatch may be modified depending on a user requirement. It may be understood that the specific embodiment described above is only a specific implementation of the present invention, and another manner in which the solution of the present invention can be implemented also fails within the protection scope of the present invention. Further details are not described herein.

Figure 3:
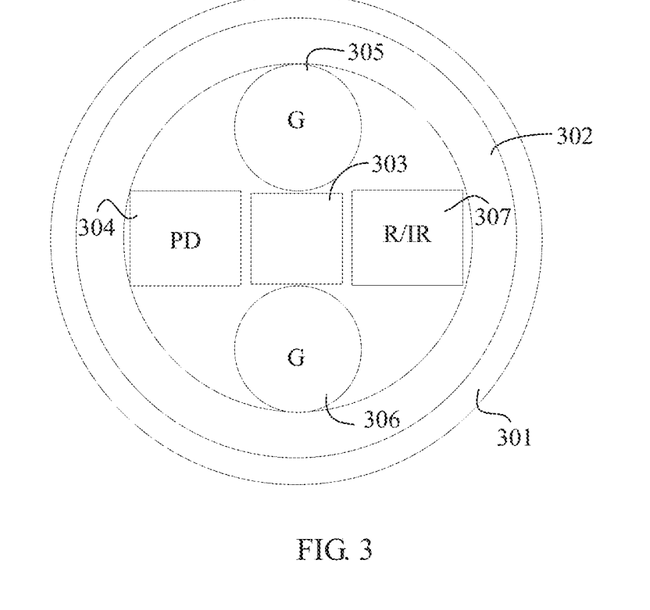
FIG. 3 is a schematic structural diagram of a smartwatch according to an embodiment of the present invention.

FIG. 3 is a schematic structural diagram of a smartwatch according to an embodiment of the present invention. As shown in FIG. 3, a detection apparatus uses a PPG method for measurement. The detection apparatus is disposed in a watch case 301, so that a user who wears a smartwatch that includes the detection apparatus uses the detection apparatus to detect information and process detected information to obtain a detection result.

Specifically, the detection apparatus includes one set of measuring parts 304 and a plurality of sets of light emitting parts 305, 306, and 307. The one set of measuring parts and the plurality of sets of light emitting parts are disposed into the case and arranged into a polygon, and a center of the polygon coincides with a center of the case. A central position of the polygon is at a specified distance to each angle of the polygon, so that the center of the case is left vacant and any other second device may be disposed in the center.

The plurality of sets of light emitting parts 305, 306, and 307 are configured to emit light. The light reaches skin of a wearer, and is reflected by hemoglobin in a blood vessel inside a human tissue. The one set of measuring parts 304 is configured to receive the light reflected by the human body. The measuring parts 304 further process the reflected light, so as to obtain the detection result.

Specifically, content of hemoglobin is related to the human pulse. The measuring parts 304 perform calculation on the collected light by using a photoplethysmograph (PPG) method to obtain oxygen saturation (SP02, Peripheral Oxygen Saturation Pulse Oxygen Saturation) and heart rate (HR) detection results.

The measuring parts 304 generate a direct current signal and an alternating current signal based on the reflected light. The direct current signal has complicated composition and usually includes reflected light of environmental light, skin, a tissue, and the like. The alternating current signal is reflected light of hemoglobin. A ratio of the alternating current signal to the direct current signal is referred to as a modulation depth. An increase of the modulation depth leads to a greater alternating current signal and a more accurate detection result.

It should be noted that the plurality of sets of light emitting parts including 305, 306, and 307 is merely an example of the present invention. In this specific embodiment of the present invention, the plurality of light emitting parts may be in any quantity of sets. The one set of measuring parts 304 and the plurality of sets of light emitting parts are arranged into a polygon, and a shape of the polygon is determined by a quantity of the plurality of sets of light emitting parts. For example, when one set of measuring parts and three sets of light emitting parts are included, the one set of measuring parts and the three sets of light emitting parts form a quadrilateral on the watch case.

In an example, a structure of the detection apparatus is shown in FIG. 3. The measuring parts 304 include one set of photodiodes (PD). The light emitting parts include three sets of light emitting diodes (LED). The three sets of light emitting diodes specifically include one set of green LEDs and two sets of red and infrared LEDs. The measuring parts 304 and the light emitting parts 305, 306, and 307 are disposed in four corners, so as to maximize a distance between the measuring parts and the light emitting parts.

This can increase the modulation depth, obtain a greater alternating current signal, and make the detection result more accurate.

It should be noted that the one set of measuring parts including one PD or one set of light emitting parts including one light emitting diode is merely an example of the present invention. The one set of measuring parts may include any quantity of PDs, and one set of light emitting parts may include any quantity of LEDs.

Figure 4:
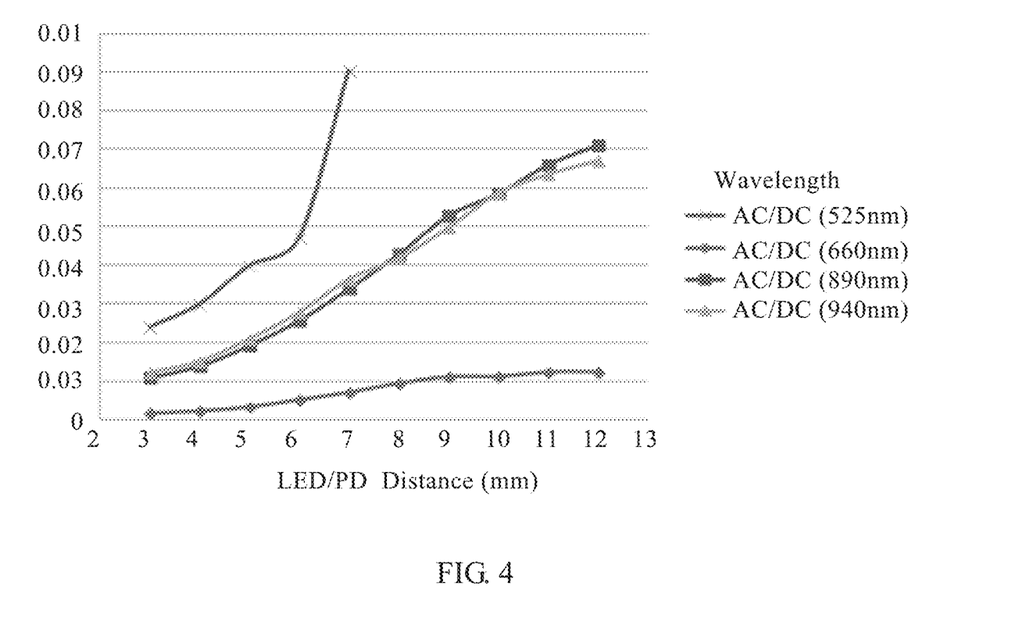
FIG. 4 is a curve diagram of modulation depths of different wavelengths and distances according to a specific embodiment of the present invention.

FIG. 4 is a curve diagram of modulation depths of different wavelengths and distances according to a specific embodiment of the present invention. As shown in FIG. 4, modulation depths of four types of light with different wavelengths and different LED-to-PD distances are included. From FIG. 4, it can be learned that, for light of different wavelengths, the modulation depth decreases with increasing of the wavelength; for light of a same wavelength, the modulation depth increases with increasing of the LED-to-PD distance.

In the example in FIG. 3 of this specific embodiment of the present invention, disposing the detection apparatus and the light emitting parts in four corners ensures a maximal distance between the detection apparatus and the light emitting parts. This makes the detection result more approximate to an actual value.

In a solution of this specific embodiment of the present invention, the smartwatch further includes a wireless charging apparatus, so that the watch may be charged by using a wireless charging device. The wireless charging apparatus includes a coil 302 and a magnet 303. Charging efficiency of the wireless charging apparatus depends on the magnet 303, and a larger area of the coil indicates higher charging efficiency. Therefore, to expand the area of the coil 302, the coil 302 is disposed on an external side of a watch case 301, and does not overlap the light emitting parts or the measuring parts. The magnet 303 is used for position locking, and the wireless charging device and the watch are position-locked by using the magnet 303. However, the magnet 303 has great influence on efficiency of the wireless charging device. A larger distance from the magnet 303 to the coil 302 indicates less influence on the wireless charging efficiency. Therefore, the magnet 303 is usually disposed at a central position of the watch, so as to increase the charging efficiency. In another solution of this specific embodiment of the present invention, the detection apparatus further includes an electrode for electrocardiograph detection, and the electrode for electrocardiograph detection is disposed at the central position of the case. Because the central position of the case is in closest contact with the skin, conductivity of the electrocardiograph electrode is increased and the electrocardiograph detection result is more accurate.

Because the detection apparatus and the light emitting parts are disposed in four corners, the central position of the watch case may be used to dispose the magnet of the wireless charging device, the electrocardiograph (ECG) electrode, or the like. When the central position of the watch case is used to dispose the magnet, the wireless charging efficiency of the device can be increased. When the central position of the watch case is used to dispose the ECG electrode, the ECG electrode can have better conductivity.

It should be noted that any second detection device may be disposed at the central position of the watch case. Because the central position is a position in best contact with the skin, in a PD-disposed detection solution, reserving the central position ensures a best installation position for any other second detection device, thereby increasing accuracy of a detection result of the second detection device.

It should be noted that the specific structure of PD, R/IR, and G disposition shown in FIG. 3 is merely an implementation of this specific embodiment of the present invention. In this specific embodiment of the present invention, different arrangement manners may be used depending on different detection solutions. For blood oxygen detection, the red/infrared (R/IR) LED is started so that the PD can perform detection based on reflected light. For heart rate detection, the green (G) LED is started so that the PD can perform detection based on reflected light. It can be hereby determined that FIG. 3 is a preferred solution for blood oxygen detection.

Figure 5A:
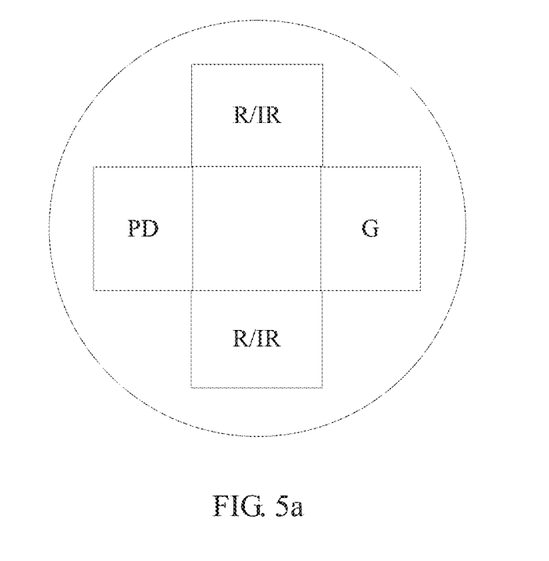
FIG. 5a is a schematic structural diagram of a first preferred detection apparatus for heart rate detection according to a specific embodiment of the present invention.

FIG. 5a is a schematic structural diagram of a first preferred detection apparatus for heart rate detection according to a specific embodiment of the present invention. As shown in FIG. 5a, one set of PDs, two sets of red/infrared LEDs, and one set of green LEDs are included. A first set of light emitting parts and a second set of light emitting parts are red/infrared LEDs, and a third set of light emitting parts are green LEDs. The first set of light emitting parts and the second set of light emitting parts are adjacent to a first set of PDs, the third set of light emitting parts are opposite to the first set of PDs, and the third set of light emitting parts are adjacent to the first set of light emitting parts and the second set of light emitting parts. The smartwatch receives a first control instruction and starts the two sets of red/infrared LEDs by using the first control instruction. The PD detects skin-reflected light to perform blood oxygen detection. The smartwatch receives a second control instruction and starts the one set of green LEDs by using the second control instruction. Because a distance between the green LEDs and the PDs is relatively large, a modulation depth is increased, making a heart rate detection result more accurate.

In this specific embodiment of the present invention, the detection apparatus of the smartwatch may further be a preferred solution for blood oxygen detection. The detection apparatus includes one set of PDs, two sets of green LEDs, and one set of red/infrared LEDs. A first set of light emitting parts and a second set of light emitting parts are green LEDs, and a third set of light emitting parts are red/infrared LEDs. The first set of light emitting parts and the second set of light emitting parts are adjacent to a first set of PDs, the third set of light emitting parts are opposite to the first set of PDs, and the third set of light emitting parts are adjacent to the first set of light emitting parts and the second set of light emitting parts.

In the foregoing solution, the smartwatch receives a first control instruction and starts the two sets of green LEDs by using the first control instruction. The PD detects skin-reflected light to perform heart rate detection. The smartwatch receives a second control instruction and starts the one set of red/infrared LEDs by using the second control instruction. Because a distance between the red/infrared LEDs and the PDs is relatively large, a modulation depth is increased, making a blood oxygen detection result more accurate.

Figure 5B:
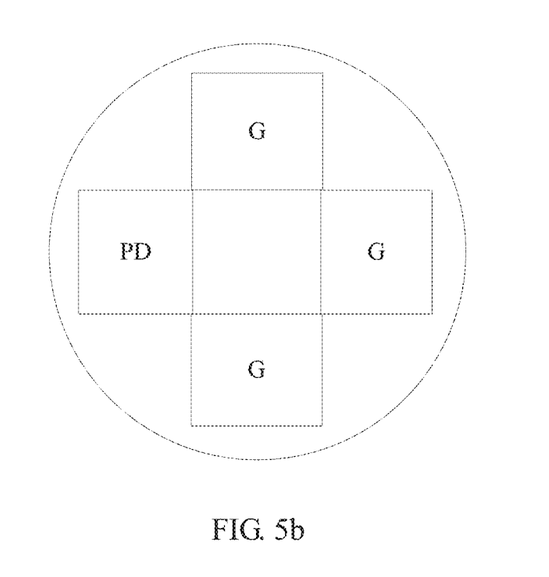
FIG. 5b is a schematic structural diagram of a detection apparatus used for heart rate detection according to a specific embodiment of the present invention.

FIG. 5b is a schematic structural diagram of a detection apparatus used for heart rate detection according to a specific embodiment of the present invention. As shown in FIG. 5b, one set of PDs and three sets of light emitting parts are included. The three sets of light emitting parts are green LEDs. A first set of light emitting parts and a second set of light emitting parts are adjacent to the one set of PDs, a third set of light emitting parts are opposite to the first set of PDs, and the third set of light emitting parts are adjacent to the first set of light emitting parts and the second set of light emitting parts. The three sets of green LEDs may be started at different moments. If a larger modulation depth is required, green LEDs at a farthest distance to the PDs need to be started. If system power consumption needs to be reduced, two green LEDs closer to the PDs may be started.

In an example, the smartwatch starts the first set of light emitting parts and the second set of light emitting parts according to a first control signal, and starts the third light emitting parts according to a second control signal. The first control signal is a signal for reducing the system power consumption and the second control signal is a signal for increasing the modulation depth.

Figure 5C:
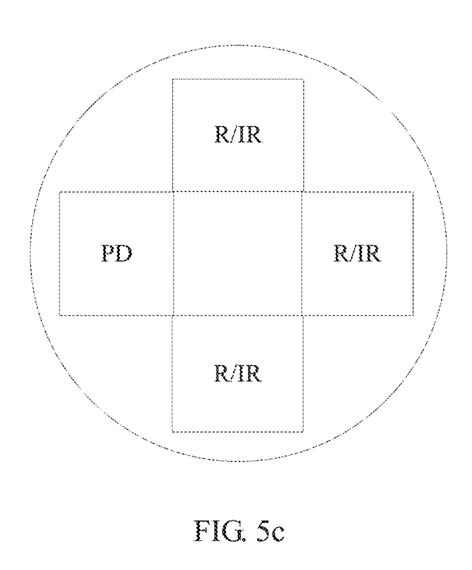
FIG. 5c is a schematic structural diagram of a detection apparatus used for blood oxygen detection according to a specific embodiment of the present invention.

FIG. 5c is a schematic structural diagram of a detection apparatus used for blood oxygen detection according to a specific embodiment of the present invention. As shown in FIG. 5c, one set of PDs and three sets of light emitting parts are included, where the three sets of light emitting parts are red/infrared LEDs. A first set of light emitting parts and a second set of light emitting parts are adjacent to the one set of PDs, a third set of light emitting parts are opposite to the first set of PDs, and the third set of light emitting parts are adjacent to the first set of light emitting parts and the second set of light emitting parts. The three red/infrared LEDs may be started at different moments. If a larger modulation depth is required, red/infrared LEDs at a farthest distance to the PDs need to be started. If system power consumption needs to be reduced, two red/infrared LEDs closer to the PDs may be started.

In an example, the smartwatch starts the first set of light emitting parts and the second set of light emitting parts according to a first control signal, and starts the third light emitting parts according to a second control signal, where the first control signal is a signal for reducing the system power consumption and the second control signal is a signal for increasing the modulation depth.

Figure 5D:
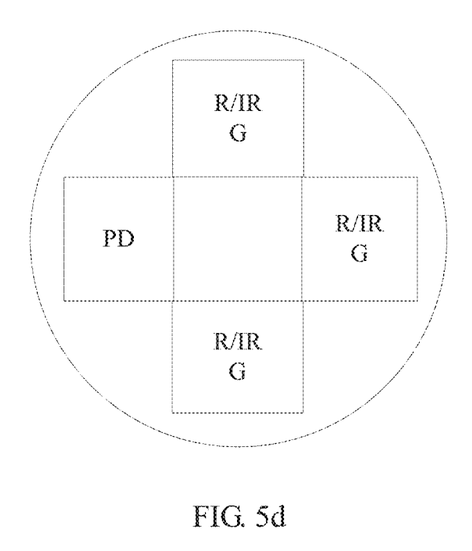
FIG. 5d is a schematic structural diagram of a detection apparatus used for both blood oxygen and heart rate detection according to a specific embodiment of the present invention.

FIG. 5d is a schematic structural diagram of a detection apparatus used for both blood oxygen and heart rate detection according to a specific embodiment of the present invention. As shown in FIG. 5d, one set of PDs and three sets of light emitting parts are included. The three sets of light emitting parts are three sets of tri-color LEDs of red, infrared, and green. In this solution, the tri-color LED may be switched on or off based on the description of FIG. 5b or FIG. 5c.

Figure 5E:
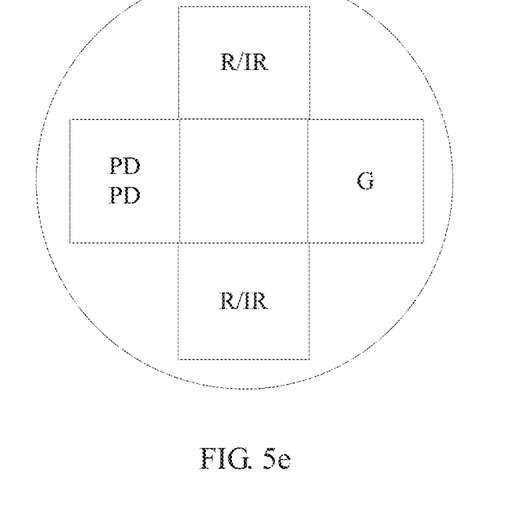
FIG. 5e is a schematic structural diagram of a multi-PD detection apparatus according to a specific embodiment of the present invention.

FIG. 5e is a schematic structural diagram of a multi-PD detection apparatus according to a specific embodiment of the present invention. As shown in FIG. 5e, one set of PDs and three sets of light emitting parts are included. The one set of PDs includes two PDs and the two PDs are disposed close to each other. It should be noted that using two PDs is merely a specific multi-PD solution, and alternatively more PDs may be used. The three LEDs include two red/infrared LEDs and one green LED. Certainly, the three LEDs may be as described in any one of FIG. 3, FIG. 5a, FIG. 5b, FIG. 5c, and FIG. 5d. By disposing a plurality of PDs in one set of PDs to reduce a PD starting time, detection efficiency of the device is increased.

Figure 6:
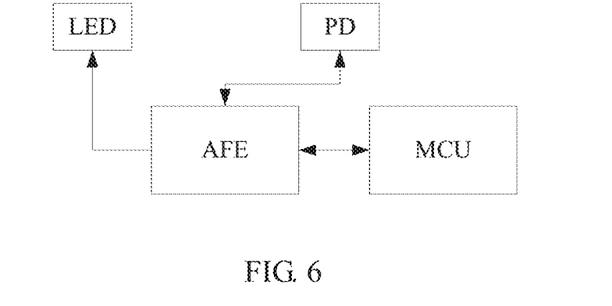
FIG. 6 is a schematic structural diagram of a detection apparatus according to a specific embodiment of the present invention.

FIG. 6 is a schematic structural diagram of a detection apparatus according to a specific embodiment of the present invention. As shown in FIG. 6, an LED, a PD, an analog front end (AFE), and a micro control unit (MCU) are included. The LED is configured to emit spectrums of different frequencies, and the spectrum is reflected by a human body, so as to generate a required optical signal. The PD is configured to receive the reflected optical signal and transform the optical signal to an electrical signal. The analog front end is configured to control work of the LED and the PD, receive the electrical signal returned by the PD, and perform preliminary processing on the electrical signal. In this specific embodiment of the present invention, the ATE may be a single component or may include a plurality of components. After performing preliminary processing on the electrical signal, the AFE returns a result to the micro control unit, and outputs a detection result based on the returned result by using the micro control unit.

Figure 7:
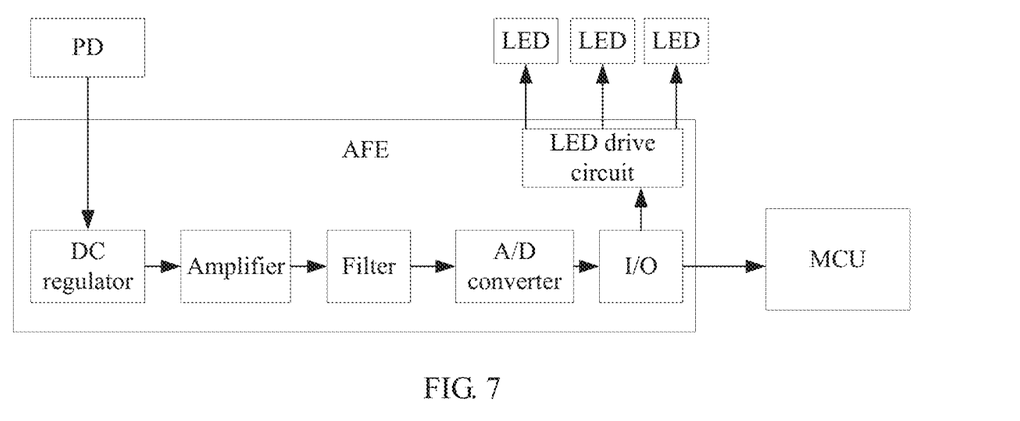
FIG. 7 is a schematic diagram of a specific structure of an AFE according to a specific embodiment of the present invention.

FIG. 7 is a schematic diagram of a specific structure of an AFE according to a specific embodiment of the present invention. As shown in FIG. 7, an I/O module, an LED drive circuit, an A/D converter, a filter, an amplifier, and a DC regulator are included.

The I/O module is connected to an MCU and receives a signal delivered by the MCU. The signal delivered by the MCU includes a signal for on-off control of an LED, and the I/O module sends the signal to the LED drive circuit. Under excitation of the current, the LED emits light of different wavelengths. Green light is usually used for heart rate detection, and a red/infrared light is usually used for blood oxygen detection. The LED drive circuit drives the LED connected to the LED drive circuit according to the signal.

The PD is connected to the DC regulation module and sends the obtained signal to the DC regulation module. The light emitted by the LED is deflected, transmitted, or reflected by the human skin, and a portion of the light enters the PD. The PD performs optical/electrical transform on the received light to obtain an electrical signal. The PD may be always in a working state, outputting only a direct current signal when the LED is not working, and outputting a direct current signal and an alternating current signal when the LED is working.

The AFE receives an alternating current signal (an analog signal) sent by the PD and the signal goes though DC regulation, amplification, filtering, A/D conversion, and the like. The AFE transforms the obtained analog signal into a digital signal, and transmits the digital signal to an MCU, a DSP, or the like. Inside the MCU, the obtained digital signal is parsed by using an algorithm, so as to obtain a heart rate value, a blood oxygen value, or the like.

In the foregoing specific implementations, the objective, technical solutions, and benefits of the present invention are described with further detail. It should be understood that the foregoing descriptions are merely specific implementations of the present invention, but are not intended to limit the protection scope of the present invention. Any modification, equivalent replacement, or improvement made without departing from the spirit and principle of the present invention should fall within the protection scope of the present invention.

What is claimed is:

1. A smart wearable device, wherein the smart wearable device comprises:
   a detection apparatus and a case, the detection apparatus comprises a set of measuring parts and at least three sets of light emitting parts;
   wherein:
   the set of measuring parts and the at least three sets of light emitting parts are inlaid into the case,
   the at least three sets of light emitting parts comprise a first set of light emitting parts, a second set of light emitting parts, and a third set of light emitting parts,
   a center of the set of measuring parts, a center of the first set of light emitting parts, a center of the second set of light emitting parts, and a center of the third set of light emitting parts form a quadrilateral,
   the first set of light emitting parts and the second set of light emitting parts are adjacent to the set of measuring parts, and the third set of light emitting parts are opposite to the set of measuring parts,
at least one of the first set of light emitting parts or the second set of light emitting parts is operable to emit green light for detecting heart rate, and
the third set of light emitting parts is configured to emit at least one of red light or infrared light for detecting blood oxygen.

2. The smart wearable device according to claim 1, wherein a second device is further disposed at a central position of the quadrilateral.

3. The smart wearable device according to claim 2, wherein the smart wearable device comprises a wireless charging device, the wireless charging device comprises an electromagnetic coil and a magnet, the electromagnetic coil is disposed at an edge of the case, and the magnet is the second device.

4. The smart wearable device according to claim 2, wherein the second device is an electrode for electrocardiograph measurement.

5. The smart wearable device according to claim 1, wherein the first set of light emitting parts comprises at least one light emitting diode; the second set of light emitting parts comprises at least one light emitting diode; the third set of light emitting parts comprises at least one light emitting diode; and the one set of measuring parts comprises at least one photodiode.

6. The smart wearable device according to claim 1, wherein each of the first set of light emitting parts, the second set of light emitting parts and the third set of light emitting parts includes at least one green diode, at least one red diode, and at least one infrared diode.

7. The smart wearable device according to claim 1, wherein the smart wearable device is operable to start at least one of the first set of light emitting parts or the second set of light emitting parts according to a first control signal, and to start the third set of light emitting parts according to a second control signal.

8. The smart wearable device according to claim 7, wherein the first control signal is a signal for reducing system power consumption, and the second control signal is a signal for increasing a modulation depth.

9. The smart wearable device according to claim 1, wherein
the first set of light emitting parts, the second set of light emitting parts, and the third set of light emitting parts are tri-color light emitting diodes of red, infrared, and green, and
the smart wearable device is operable to start the first set of light emitting parts and the second set of light emitting parts according to a first control signal or a third control signal, and to start the third set of light emitting parts according to a second control signal or a fourth control signal, wherein the first control signal is a blood oxygen detection signal for reducing system power consumption, the second control signal is a blood oxygen detection signal for increasing a modulation depth, the third control signal is a heart rate detection signal for reducing system power consumption, and the fourth control signal is a heart rate detection signal for increasing a modulation depth.

10. The smart wearable device according to claim 1, wherein the smart wearable device is a smartwatch.

11. The smart wearable device according to claim 10, wherein the smartwatch is operable to:
receive a first control instruction to start the first set of light emitting parts and the second set of light emitting parts and to detect a reflected light by the set of measurement parts, so as to detect heart rate; or
receive a second control instruction to start the third set of light emitting parts and to detect reflected light by the set of measurement parts, so as to detect blood oxygen.

12. The smart wearable device according to claim 1, wherein the smart wearable device is operable to:
send green light for detecting heart rate by turning on at least one of the first set of light emitting parts or the second set of light emitting parts during heart rate detection, wherein the set of measuring parts is operable to detect heart rate according to reflected light; and
send at least one of red light or infrared light for detecting blood oxygen by turning on the third set of light emitting parts during blood oxygen detection, wherein the set of measuring parts is operable to detect blood oxygen according to the reflected light.

13. A smart wearable device, wherein the smart wearable device comprises:
a detection apparatus and a case, the detection apparatus comprises a set of measuring parts and at least three sets of light emitting parts;
wherein:
the set of measuring parts and the at least three sets of light emitting parts are inlaid into the case,
the at least three sets of light emitting parts comprise a first set of light emitting parts, a second set of light emitting parts, and a third set of light emitting parts,
a center of the set of measuring parts, a center of the first set of light emitting parts, a center of the second set of light emitting parts, and a center of the third set of light emitting parts form a quadrilateral,
the first set of light emitting parts and the second set of light emitting parts are adjacent to the set of measuring parts, the third set of light emitting parts is opposite to the set of measuring parts,
each of the first set of light emitting parts, the second set of light emitting parts and the third set of light emitting parts includes one green diode, one red diode, and one infrared diode,
one of the first set of light emitting parts or the second set of light emitting parts is operable to emit green light for detecting heart rate, and
the first set of light emitting parts, the second set of light emitting parts and the third set of light emitting parts are operable to emit red light and infrared light for detecting blood oxygen, wherein the red diode of the first set of light emitting parts, the red diode of the second set of light emitting parts and the red diode of the third set of light emitting parts emit red light at different moments, and the infrared diode of the first set of light emitting parts, the infrared diode of the second set of light emitting parts and the infrared diode of the third set of light emitting parts emit infrared light at different moments.

14. The smart wearable device according to claim 13, wherein the set of measuring parts comprises at least one photodiode.

15. The smart wearable device according to claim 13, wherein
the smart wearable device is operable to start one of the first set of light emitting parts or the second set of light emitting parts according to a first control signal, and to start one of the first set of light emitting parts, the second set of light emitting parts or the third set of light emitting parts according to a second control signal.

16. The smart wearable device according to claim 15, wherein the first control signal is a signal for reducing system power consumption, and the second control signal is a signal for increasing a modulation depth.

17. The smart wearable device according to claim 13, wherein the smart wearable device is a smartwatch.

18. The smart wearable device according to claim 17, wherein the smartwatch is operable to:
  receive a first control instruction to start the first set of light emitting parts or the second set of light emitting parts and to detect reflected light by the one set of measurement parts, so as to detect heart rate; or
  receive a second control instruction to start one of the first set of light emitting parts, the second set of light emitting parts and the third set of light emitting parts and to detect a reflected light by the one set of measurement parts, so as to detect blood oxygen.

19. The smart wearable device according to claim 13, wherein the smart wearable device is operable to:
  send green light for detecting heart rate by turning on the first set of light emitting parts or the second set of light emitting parts during heart rate detection, wherein the set of measuring parts is operable to detect heart rate according to a reflected light; and
  send at least one of red light or infrared light for detecting blood oxygen by turning on one of the first set of light emitting parts, the second set of light emitting parts or the third set of light emitting parts during blood oxygen detection, wherein the set of measuring parts is operable to detect blood oxygen according to the reflected light.

20. The smart wearable device according to claim 13, wherein a second device is further disposed at a central position of the quadrilateral.

* * * * *